United States Patent [19]

Draenert

[11] Patent Number: 5,047,030

[45] Date of Patent: Sep. 10, 1991

[54] SUCTION DRAINAGE-BONE SCREW

[76] Inventor: Klaus Draenert, Gabriel-Max-Str. 3, DE-8000 München 90, Fed. Rep. of Germany

[21] Appl. No.: 541,099

[22] Filed: Jun. 20, 1990

Related U.S. Application Data

[63] Continuation of Ser. No. 272,749, filed as PCT EP88/00122 Feb. 19, 1988, published as WO88/06023, Aug. 25, 1988, abandoned.

[30] Foreign Application Priority Data

Feb. 20, 1987 [DE] Fed. Rep. of Germany .... 3705541

[51] Int. Cl.$^5$ ............................................. A61F 5/04
[52] U.S. Cl. .............................................. 606/65; 606/73
[58] Field of Search ................... 606/60, 62, 64, 65, 606/68, 73, 77, 80, 104, 72

[56] References Cited

U.S. PATENT DOCUMENTS

| | | | |
|---|---|---|---|
| 2,242,003 | 5/1941 | Lorenzo | 606/73 |
| 2,243,717 | 5/1941 | Moreira | 606/104 |
| 2,248,054 | 7/1941 | Becker | 606/14 |
| 2,267,925 | 12/1941 | Johnston | 606/73 |
| 2,532,296 | 12/1950 | Giesen | 606/73 |
| 2,570,465 | 10/1951 | Lundholm | 606/73 |
| 2,614,559 | 10/1952 | Livingston | 606/64 |
| 2,631,584 | 3/1953 | Purificato | 606/73 |
| 3,103,926 | 9/1963 | Cochran | 606/73 |
| 3,892,232 | 7/1975 | Neufeld | 606/73 |
| 4,175,555 | 11/1979 | Herbert | 606/73 |
| 4,356,572 | 11/1982 | Guillemin | 606/77 |
| 4,463,753 | 8/1984 | Gustilo | 606/73 |
| 4,537,185 | 8/1985 | Stednitz | 606/73 |
| 4,622,959 | 11/1986 | Marcus | 606/64 |
| 4,858,603 | 8/1989 | Clemow | 606/72 |

FOREIGN PATENT DOCUMENTS

| | | |
|---|---|---|
| 0172130 | 2/1986 | European Pat. Off. |
| 2015346 | 2/1979 | United Kingdom |
| 2157177 | 2/1985 | United Kingdom |

Primary Examiner—Robert A. Hafer
Assistant Examiner—Michael Brown
Attorney, Agent, or Firm—Kinney & Lange

[57] ABSTRACT

The invention relates to a bone screw (10) which can be anchored in the bone in a firm and vacuum-tight manner, and to the use of the same in arthroplastic surgery and as a drug delivery system. The interior of the bone screw (10) has a continuous longitudinal bore (15) through which the medullary canal can be evacuated during the application of bone cement. The use of the bone screw renders it possible to fill the spongiosa honeycombs with bone cement without endangering the life of the patient.

10 Claims, 4 Drawing Sheets

SUCTION DRAINAGE-BONE SCREW

This is a continuation of application Ser. No. 07/272,749 filed as PCT EP88/00122 Feb. 19, 1988, published as WO88/06023, Aug. 25, 1988, abandoned as of the date of this application.

BACKGROUND OF THE INVENTION

1. Field of the Invention

The invention relates to a bone screw which can be anchored in the bone in a firm and vacuum-tight manner, and to the use of the same in a method of applying bone cement and as a drug delivery system.

2. Description of the Prior Art

In arthroplastic surgery, most implants are inserted in the bony bed using so-called bone cement. This bone cement is usually made of polymethylmethacrylate or related compounds. However, the bone cement can only penetrate into the honeycombs of the bone marrow if they are clean and free of fat marrow and cell components.

In the prior art one therefore attempted to wash the bony bed and apply the bone cement under pressure. This technique, also called the "bone lavage and high-pressurizing technique", was usually used when applying bone cement of a low viscosity.

This technique, however, led to a number of incidents which ended fatally. Studies on animals and clinical examinations both showed that an increase in intramedullary pressure can lead to reflex cardiac arrest and that it is also possible for fatal fat and bone marrow emboli to occur. Furthermore, this method did not succeed in keeping the bony bed free of blood. On the contrary, depending on the blood pressure, the blood flowed into the bony bed and mingled with the bone cement, thus greatly impairing its qualities; this happened every time the intramedullary pressure (IMP) dropped below the blood pressure level.

Attempts have also been made to improve the bone cement used in clinics via mechanical stabilization and prepressurization. This improvement can only be completely successful in the technique of cementing if the achieved material stabilization in the bone cement can be transferred to the bony bed of the patient without endangering his life.

SUMMARY OF THE INVENTION

It is the primary object of the invention to provide a method of applying bone cement in which said bone cement is applied deeply and in an artefact-free manner around the prosthesis without endangering the life of the patient.

It is another object of the invention to provide a bone screw which can be firmly anchored in the bone and allows drainage of the medullary canal whilst the bone cement is being applied.

It is a further object of the invention to provide a bone screw which can be used as a drug delivery system.

The invention provides a method for draining the floor and/or roof of the anchorage bed which renders the bed free of blood. As known from the ASIF (Association for Studying Internal Fixation), conventional bone screws, the thread of which has been adapted to the individual load transmission, can achieve a tight sealing of the bone canal. This can be achieved with both pre-cut threads and tapping screws. The bone screw of the invention has an axially continuous longitudinal canal or bore in its interior and is adapted to receive a vacuum line in the appropriate manner in the vicinity of the screw head. Thus it is possible to suck the blood and fat out of the bone canal and the area around it through the longitudinal canal of the bone screw.

The invention also provides a bone screw which can be anchored in the bone in a firm and vacuum-tight manner and has a continuous longitudinal canal in its interior.

According to the invention, said bone screw is used for sucking blood, fat or bone marrow out of the bone canal and the area around it, especially when working with bone cement in arthroplastic surgery. The bone screw of the invention can also be used as a "drug delivery system", the active agent preferably being an antibiotic in a carrier substance or a cytostatic drug. Using two cannulated screws, one for drainage and one for perfusion, it is possible to perform a drug perfusion technique, for example to locally treat a metastasis in the bone.

The bone screw of the invention renders it possible to fill the bone canal with bone cement under vacuum. It is absolutely imperative to fill in the spongiosa with bone cement in the areas in which it is under load in order to reinforce the framework against deformation. The distal draining and drying of the bony bed and the method of sucking the bone cement deep into the femur allows complete and artefact-free filling of the cement around the prosthesis. Once the medullary canal has been filled in, the proximal metaphysal spongiosa is drained separately. Due to its morphology, the spongiosa has to be opened up from the interior via drilling canals so that the spongiosa honeycombs can be filled with cement up to the level of the compact substance and thus almost completely reinforced against deformation. The bone marrow is prevented from being sucked off through the suction syringe of the bone screw by a cortico-spongious plug which acts as a filter. The plug is removed and distally displaced when the medullary canal is opened. By using the bone screw of the invention with its longitudinal canal, it is possible to fill in the proximal spongiosa honeycombs via opening canals and under moderate pressure and complete relief of pressure by means of the applied vacuum. In this case, the absolute pressure applied to the medullary canal is, for instance, 100 to 150 mbar.

Via the vacuum which builds up during draining, the bone cement is sucked deep down into the bone canals and contains no air bubbles. The result is that the obtained bone bed is made of highly compact material.

The bone screw of the invention preferably exhibits one or several transverse canals, preferably two to nine, more preferably four to six, which contact the longitudinal canal, preferably extend in the approximate radial direction of the screw and open up to the outside. This leads to a further increase in the effect of the partial vacuum, especially if the diameter of the partial canals decreases the greater their distance from the tip of the screw.

The thread of the screw is preferably a tapping screw. In the region of the first three thread turns, the screw extends conically towards its tip. The first three turns are designed as thread cutters with chip-removal canals and cut the thread in the bone. This leads to a particularly tight sealing of the bone.

The dimension of the bone screw varies according to its use. When used as a cannulated bone screw in the greater trochanter and the medullary canal of the femur, in particular for applying a vacuum to such a bone cement in the bone, the screw preferably has an outer diameter of about 5 to 6.5 mm, more preferably 5.8 mm, a core hole diameter of about 4 to 5 mm, more preferably 4.5 mm, a thread length of 15 to 25 mm, more preferably 20 mm, and a pitch (lead) of 1.5 to 2.5 mm, more preferably 2 mm. The thread is preferably a breech block thread or a saw-tooth thread, the saw teeth of the thread being inclined towards the longitudinal axis at an angle of preferably about 45°. The diameter of the inner longitudinal canal or bore is about 2.5 to 3.5 mm, preferably 3 mm.

When the cannulated bone screw is used in infusion, transfusion and perfusion techniques, the diameter of the inner longitudinal canal or bore is preferably about 1 to 3 mm, more preferably between about 1.5 and 2.5 mm. Accordingly, the other dimensions of the screw can be smaller than when the screw is used for applying a vacuum to suck bone cement into the bone.

When the cannulated bone screw is used as a drug delivery system, the diameter of the inner longitudinal canal or bore is preferably about 0.6 to 1.0 mm, more preferably about 0.8 mm. In this technique, the drug preferably exhibits a cylindrical shape, and its diameter is adapted to the diameter of the inner longitudinal canal of the screw with the result that the drug can be pushed through the canal from the outside to the inside where it is applied.

The screw preferably exhibits a tubular piece with a length of about 150 to 250 mm, preferably about 200 mm, attached to the thread portion, through which piece the inner longitudinal canal of the screw extends. A removable handle with which the bone screw can be screwed into the bone is attached to the rear end of the tubular piece by a spring and a set screw. Furthermore, this site also exhibits a connection piece for a vacuum tube which leads to a sterilisable pump.

The screw is preferably made of an extremely pure surgical steel, such as V4A steel, or of titanium or a titanium alloy.

If the bone screw is to remain in the body, at least part of it, preferably the whole screw, should be made of an absorbable material. This material is preferably a plastic material or a completely resorbable material. Such materials are, for instance, described in EP-A-86 90 0132. Examples of such materials are polylactide, polyglycolide or another polyamino acid. The material can be made of a composite of an absorbable matrix and a filler, the filler preferably being a sintered hydroxylapatite or tricalciumphosphate or a finely dispersed Ca-phosphate compound.

When used as a drug delivery system, a plug located at the outer side is preferably used to hermetically seal the longitudinal canal of the screw once the drug has been inserted.

In order to reduce its weight, the handle is preferably made of Al or an Al alloy.

BRIEF DESCRIPTION OF THE DRAWINGS

The following drawings and examples illustrate the invention in greater detail.

DETAILED DESCRIPTION OF THE PREFERRED EMBODIMENTS

Figure 1:
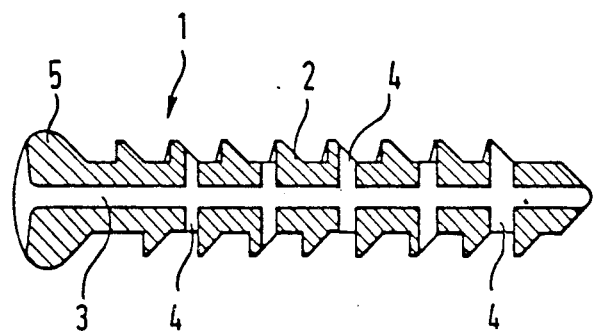
FIG. 1 is a cross section of a first embodiment of the bone screw of the invention.

FIG. 1 is a first simple embodiment of a bone screw 1 of the invention. The screw 1 has an external thread 2 which is designed as a breach block thread, the foremost edge of the saw teeth being inclined towards the longitudinal axis of the screw at an angle of about 45°. The interior of the screw 1 has a continuous longitudinal canal 3 along with several radially extending transverse canals 4 which contact the longitudinal canal 3. It is possible to appropriately connect a vacuum pump via a tube in the area around the screw head 5. In order to be able to apply the vacuum in a uniform manner, the diameter of the transverse canals increases the greater their distance from the head 5 of the screw where the vacuum pump is connected.

Figure 2A:
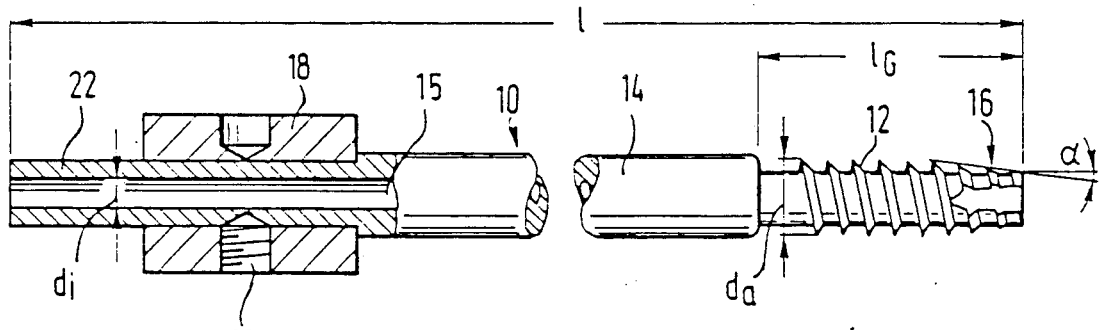
FIG. 2 is a partially cut second embodiment of the bone screw of the invention.
Figure 2B:
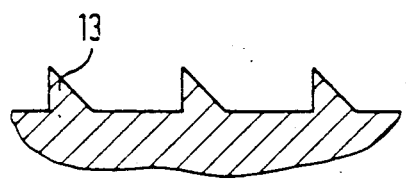

The bone screw 10 according to FIG. 2A has a thread portion 12 at its front and a tubular piece 14. The total length 1 is about 120 mm, the length $1_G$ about 20 mm. The external diameter $d_a$ of the threads is about 5.8 mm, whereas the core diameter is about 4.5 mm. Through the complete length of the bone screw 10 extends a continuous inner longitudinal canal 15, the diameter $d_i$ of which is about 3 mm. The tip of the thread is designed as a thread cutter. For this purpose, the tip 16 of the thread portion 12 tapers at an angle $\alpha$ of about 5° to 10°, preferably about 7°, and the first three thread turns of the thread portion are designed as cutters. Furthermore, chip-removal canals are provided. A sleeve 18 with a groove 20 is provided at the rear end of the tubular portion 14. A handle (not shown) is mounted onto the sleeve 18, which handle is secured via a spring with a set screw which engages with the groove 20. Furthermore, a connection piece 22 for a vacuum tube (not shown) is provided at the rear end of the bone screw 10, which tube leads to an evacuatable pump. FIG. 2B shows an enlarged section of the thread portion 12, wherein the threads 13 are designed as saw teeth. The edges of the teeth are inclined at an angle of approximately 45° and 87°, respectively, with regard to the screw axis.

Figure 3:
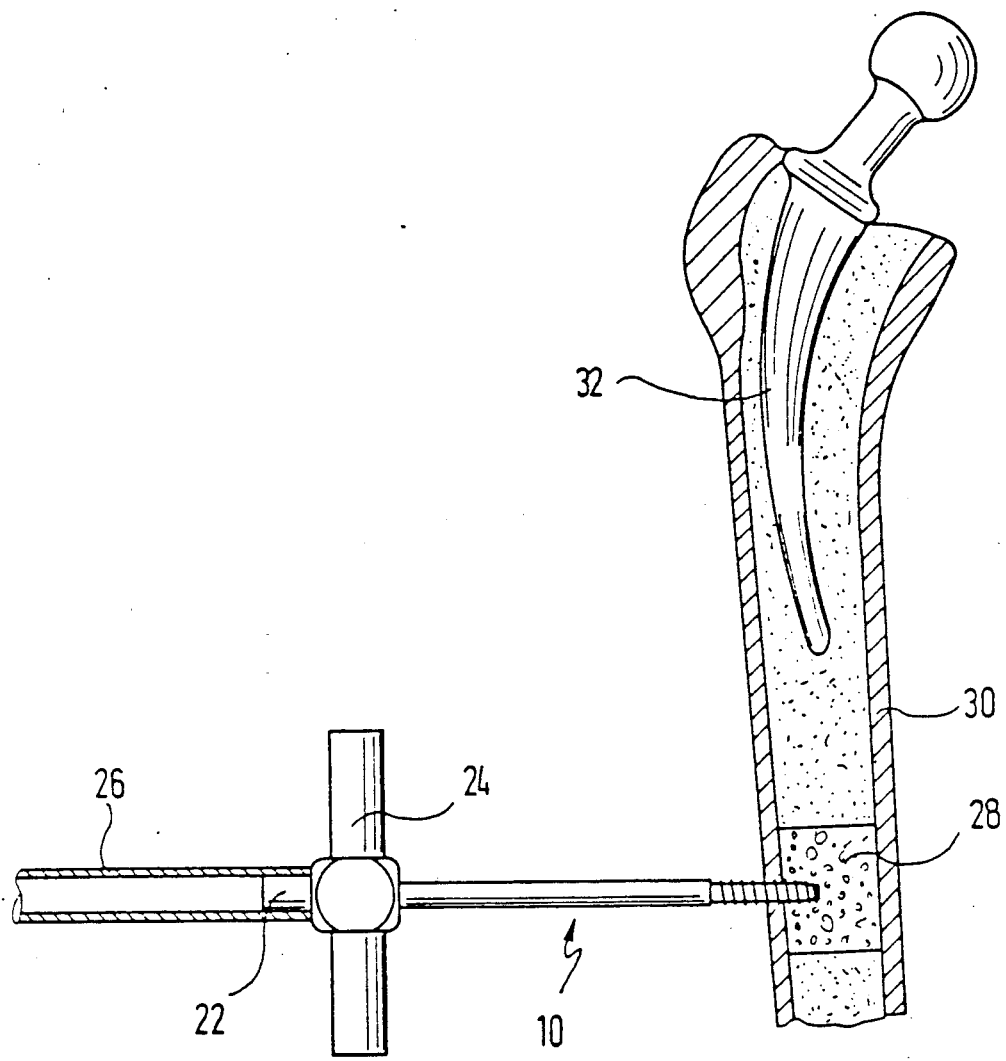
FIG. 3 is the arrangement of a bone screw of the invention for draining the medullary canal of the femur.

FIG. 3 shows the arrangement of a bone screw 10 of the invention for draining the medullary canal of the femur. This technique will be explained in greater detail in the examples. FIG. 3 shows the handle 24 at the rear end of the screw, through which handle the screw 10 is to be turned. The vacuum tube 26 which leads to the pump is mounted on the connection piece 22 at the rear end of the screw 10. FIG. 3 also shows that the screw 10 is inserted into a cortico-spongious plug 28 in the femur 30 below a prosthesis 32.

Figure 4:
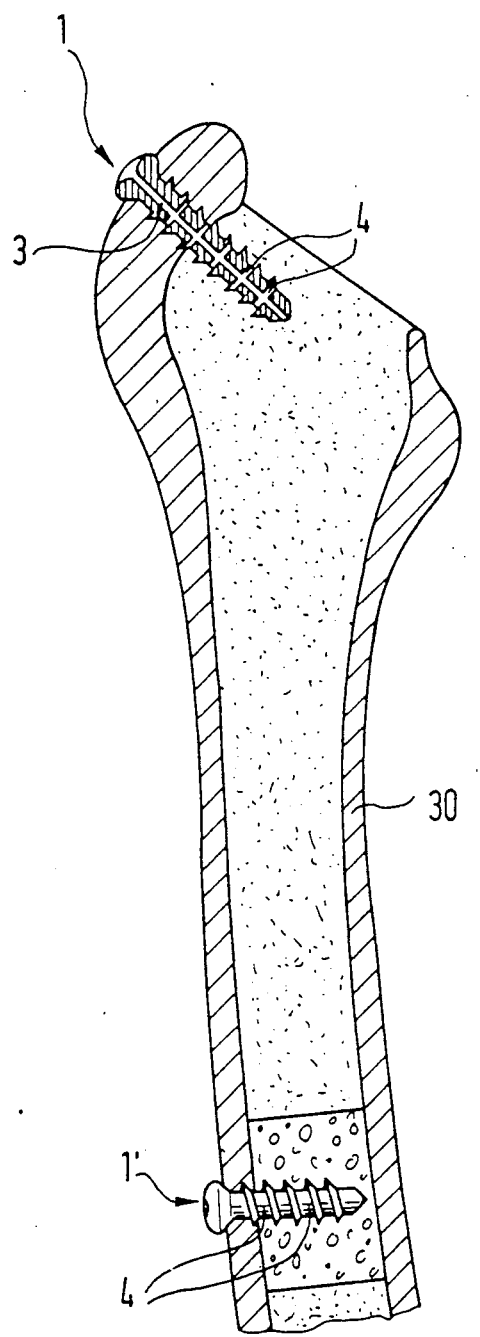
FIG. 4 is the arrangement of two bone screws of the invention in the greater trochanter and the medullary canal of the femur.

FIG. 4 is a systematic illustration of a cannulated bone screw 1' inserted for the distal draining of the medullary canal of the femur 30 and a proximally inserted cannulated bone screw 1 in the greater trochanter. This technique, too, will be explained in greater detail in the examples. FIG. 4 shows a cross section of the proximal bone screw 1 and a side view of the distal bone screw 1' inserted into a cortico-spongious plug 28.

The following examples illustrate the invention.

EXAMPLE 1

In order to demonstrate the manner in which the femur is drained, an experiment is carried out in which the corroded, soft tissue-free femur and its canal system are welded into a film in such a manner that the area surrounding the femur can be evacuated. The femur is then filled with dye, followed by periostally applying a vacuum in the film and noting the time it takes for the dye to pass out of the medullary canal and into a collecting vessel via a tube. It was shown that within three seconds the dye is sucked out of the medullary canal only through the canal systems located along the linea aspera. For the rest of the experiment it suffices to seal the metaphysial region of the femur and the linea aspera with a transparent varnish in order to achieve a high vacuum in the medullary canal. A cannulated bone screw is then anterolaterally inserted into the femur 2 cm beneath the site which corresponds to the tip of the implanted metal prosthesis. The process of evacuation is carried out via the longitudinal canal of the bone screw with the result that a vacuum with an absolute pressure of about 100 to 150 mbar builds up. The femur is then proximally sealed with silicone rubber and the bone cement applied from the proximal direction to the distal direction. This is followed by the insertion of a plastic replica of a Müller standard prosthesis, a damp compress being used to prevent the bone cement from being proximally pressed out. In a second experiment, drainage is carried out in several femora both distally and proximally at the same time. In this case, the proximal, cannulated bone screw is laterally inserted at the greater trochanter in the direction of the lesser trochanter. Evacuation is carried out with the same intensity in both screws. The filling and insertion of the prosthesis is carried out in the same way.

The results of these experiments show that the distal application of vacuum leads to a "water-tight" bone cement filling from the region of the shaft up to the transition of the metaphysis. However, in the region in which deep penetration of the bone cement into the spongiosa framework is aimed at, the bone cement does not penetrate further into the spongiosa framework than it would have done as a result of the pressure exerted by the prosthesis alone without the application of a vacuum.

In the last experimental arrangement with the vacuum in the proximal metaphysis, when the bone cement has been applied, a shunt formation appears in the form of an air canal along the shaft of the prosthesis between the proximal and distal vacuum. The greater suction power is found to be on the distal side. This leads to the conclusion that the proximal, cannulated screw has a substantially smaller suction effect on the medullary canal than the distal screw which extends directly into the medullary canal.

EXAMPLE 2

In an experimental arrangement, the decrease in vacuum in the proximal metaphysis is measured after a vacuum has been distally applied to the medullary canal. Seven surface drilling holes are drilled at each the lesser trochanter, the calcar femoris and the trochanter along the dorsal, medial, foremost and lateral circumference. Measuring probes are pushed through these holes in steps of 5 mm in the direction of the medullary canal. These measurements are carried out independently at all three levels. Once the measurements have been carried out, the drilling holes are refilled with a plastic material.

These measurements yield interesting and surprising findings. They are extremely informative as regards the application of cement under high pressure, but can be explained by the development and growth pattern of the bone.

The proximal metaphysis is characterised by the fact that starting from the medullary canal, the vacuum decreases rapidly up to the metaphysial compacta to a value around atmospheric pressure, i.e. the medullary spaces of the spongiosa are not drained in the direction of the medullary canal, but in the direction of the periosteum.

The effect of the high vacuum on the coronary circulation is examined in animal experiments. To begin with, a vacuum of 100 mbar absolute pressure is applied via an opening canal in the patellar groove of one animal via a cannulated bone screw which has been inserted in a vacuum-tight manner in the bone. The respiratory rate and pulse rate are monitored. The connections between the honeycombs of the medullary space become more and more narrow towards the medullary canal, and broader and broader towards the periosteum. The measurements show a typical increase in pressure from the medullary canal towards the compacta.

EXAMPLE 3

In order to examine the cementing technique in the proximal methaphysis of the femur, in a further series of experiments several femora are opened up from the medullary canal by drilling three medial and three medio-dorsal holes with a 6 mm drill. This is followed by inserting a cannulated bone screw into the greater trochanter, which screw extends towards the lesser trochanter. As in the above examples, a cannulated bone screw is anterolaterally inserted into the cortical bone 2 cm distal of the tip of the prosthesis. The distal screw is placed into a cortico-spongious plug to ensure that the distal and proximal medullary canal remain delimited from the screw by means of a spongiosa filter. A synthetic or manufactured filter or plug may be used instead of the cortico-spongious plug. The bone is filled with Palacos R ® bone cement mixed under vacuum. Prior to application, the bone cement and the mixing vessels are cooled to 1° C. The temperature of the mixture when applied to the femur is between 18° and 22° C. The femur is proximally sealed with silicone rubber. After having been precompressed or prepressurized, the bone cement is applied to the femur at the beginning of the fourth minute of the mixing phase. The bone cement is sucked deep down into the femur by the vacuum applied via the distal, cannulated bone screw. Once the prosthesis component has been inserted, the distal vacuum lead is pinched off and the vacuum proximally applied. The silicone rubber prevents the bone cement from being pressed out. The vacuum remains effective in the metaphysis until the bone cement has hardened.

The preparations are sawed open. They reveal that the distal segments of the medullary canal of the proximal half of the femur are completely filled with bone cement and that the peripheral spongiosa honeycombs are totally reinforced by bone cement. Proximally the cement has advanced to the calcar femoris, laterally it has penetrated approximately 4 to 5 mm into the framework of the cancellous bone.

The comparison between filling from the proximal to the distal direction and filling from the distal to the proximal direction using a nozzle shows that only with distal suction and proximal application of the bone cement can the spongiosa honeycombs be filled and the mingling in of blood be avoided. In the other methods of application, liquid is pushed along the interface from the distal to the proximal direction, and very often, depending on the viscosity of the bone cement, the liquid will be pushed into the cement mass thus causing lamination and the formation of haematocysts. This, in turn, greatly decreases the stability of the bone cement.

EXAMPLE 4

The effect of high vacuum on the coronary circulation is examined in animal experiments. To begin with, a vacuum of 100 mbar absolute pressure is applied via an opening canal in the patellar groove of one animal via a cannulated bone screw which has been inserted in a vacuum-tight manner in the bone. The respiratory rate and pulse frequency are monitored.

It can be seen that no blood is sucked out of the canals once a small amount of the content of the medullary space has been sucked off. The respiratory rate and pulse frequency remain completely unchanged.

EXAMPLE 5

Further experiments show that centripetal application via the cannulated bone screw can be used in the treatment of bone affections. It is shown that over a certain period of time, active agents in a matrix located in the canals of the screw can achieve extremely high concentrations at the site of application. As the bone screw seals the bone in a hermetic manner, the active substance cannot be retrogradely lost. Furthermore, precise insertion of the screw is possible. The bone screw of the invention can thus also be used as a "drug delivery system".

EXAMPLE 6

The bone screw of the invention can also be used in a highly effective local treatment applied, for instance, in osteomyelitis and bone tumors. The first cannulated screw is used to apply a drug at high concentrations directly in or next to the site of focal disease, and the second cannulated screw is used to suck off the perfusion liquid in the vicinity of the focal disease in order to avoid penetration of the drug into the circulation.

Figure 5:
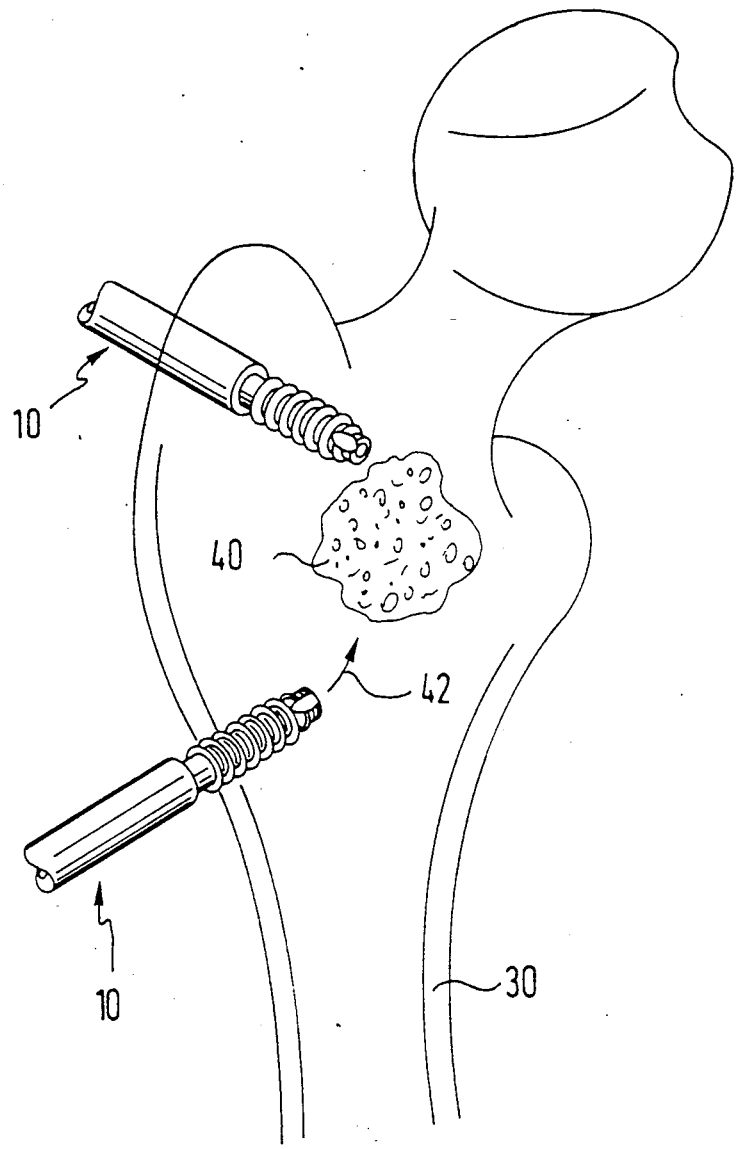
FIG. 5 shows a perspective view of the arrangement of two bone screws of the invention used for perfusion purposes.

FIG. 5 shows a perspective view of such an arrangement. In FIG. 5, two cannulated screws 10 are arranged closely above and below a metastasis 40 in the femur 30. The two screws 10 are preferably inserted in different directions, preferably at an angle of 90° to 180° with respect to one another. The perfusion liquid or drug is applied via the lower bone screw and is sucked through the longitudinal canal of the upper bone screw which is connected to a vacuum line (not shown). The arrow 42 shows the flow of the perfusion liquid. Such a perfusion can be applied for several days. In order to facilitate its insertion, the tip of the bone screw of the invention can additonally comprise a self-cutting drill.

I claim:

1. A bone screw to be firmly anchored in bone in an essentially vacuum-tight manner, the bone screw comprising:
   a threaded portion at a front end of the bone screw, the threaded portion having a core diameter;
   a tubular member connected to the threaded portion, the tubular member having a diameter greater than the core diameter of the threaded portion;
   a sleeve portion provided at a rear end of the tubular member opposite the threaded portion, the sleeve portion adapted to be engaged by a handle;
   a connection piece for a connecting a vacuum line to the tubular member, the connection piece being provided at the rear end of the tubular member adjacent the sleeve portion; and
   a longitudinal bore through the length of the bone screw.

2. The bone screw according to claim 1, having one or several transverse bores which contact the longitudinal bore.

3. The bone screw according to claim 1, wherein the tip of the thread of the screw is designed as a thread-forming screw.

4. The bone screw according to claim 1, wherein the screw is made of an extremely pure surgical steel or of titanium or a titanium alloy.

5. The bone screw according to claim 1, wherein at least part of the screw is made of an absorbable material.

6. The bone screw according to claim 1, wherein the screw has an outer diameter of about 5 to 6.5 mm, the core diameter is about 4 to 5 mm, a thread pitch of about 1.5 to 2.5 mm and a thread length of about 15 to 25 mm.

7. The bone screw according to claim 1, wherein the longitudinal bore has a diameter of about 2.5 to 3.5 mm.

8. The bone screw according to claim 1 for use in sucking blood, fat and bone marrow out of the bone canal and its vicinity and for suction drainage in the application of bone cement.

9. The bone screw according to claim 1 for use as a "drug delivery system".

10. The bone screw according to claim 9, wherein the screw can be closed at the outside.

* * * * *